US007803980B2

(12) United States Patent
Griffiths et al.

(10) Patent No.: US 7,803,980 B2
(45) Date of Patent: Sep. 28, 2010

(54) MULTI-LAYERED WOUND DRESSING

(75) Inventors: Bryan Griffiths, Chester (GB); David C. Pritchard, Chester (GB); Elizabeth Jacques, Chester (GB); Steven M. Bishop, Deeside (GB); Michael Lydon, Sychdyn (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 0 days.

(21) Appl. No.: 10/883,205

(22) Filed: Jul. 1, 2004

(65) Prior Publication Data

US 2004/0236260 A1    Nov. 25, 2004

Related U.S. Application Data

(62) Division of application No. 09/904,189, filed on Jul. 12, 2001, now Pat. No. 6,793,645.

(30) Foreign Application Priority Data

Jul. 12, 2000 (GB) .................................. 0017080

(51) Int. Cl.
*A61F 13/00* (2006.01)
*A61F 13/15* (2006.01)
*A61F 13/20* (2006.01)
*A61F 15/00* (2006.01)

(52) U.S. Cl. ............................. 602/52; 602/42; 602/43; 602/54; 604/304; 604/358

(58) Field of Classification Search ............. 602/41–59; 536/63; 604/304, 358
See application file for complete search history.

(56) References Cited

U.S. PATENT DOCUMENTS

| | | | | | |
|---|---|---|---|---|---|
| 4,461,668 | A | * | 7/1984 | Samuelsen | 156/543 |
| 4,906,240 | A | * | 3/1990 | Reed et al. | 604/307 |
| 4,995,382 | A | * | 2/1991 | Lang et al. | 602/55 |
| 5,412,035 | A | * | 5/1995 | Schmitt et al. | 525/93 |
| 5,681,579 | A | * | 10/1997 | Freeman | 424/448 |
| 5,840,052 | A | * | 11/1998 | Johns | 602/54 |
| 6,075,177 | A | * | 6/2000 | Bahia et al. | 602/56 |
| 6,153,214 | A | * | 11/2000 | Horsler | 424/443 |
| 6,171,594 | B1 | * | 1/2001 | Nielsen | 424/744 |
| 6,793,645 | B2 | * | 9/2004 | Griffiths et al. | 602/54 |

FOREIGN PATENT DOCUMENTS

| | | | |
|---|---|---|---|
| EP | 0 099 748 A | | 2/1984 |
| EP | 279118 A2 | * | 8/1988 |
| EP | 304536 A2 | * | 3/1989 |
| EP | 0 538 917 A | | 4/1993 |
| WO | 95 19795 A | | 7/1995 |
| WO | WO 9602284 A1 | * | 2/1996 |
| WO | 00 01425 A | | 1/2000 |
| WO | WO 0001425 A1 | * | 1/2000 |
| WO | 00 41661 A | | 7/2000 |

* cited by examiner

*Primary Examiner*—Melanie J Hand
(74) *Attorney, Agent, or Firm*—John M. Kilcoyne

(57) ABSTRACT

A multi layered wound dressing which comprises an adhesive layer, an absorbent layer overlying said adhesive layer on the surface furthest from the wound, and a moisture transmitting cover layer overlying the absorbent layer, the dressing having a total thickness of less than 1.5 mm.

20 Claims, No Drawings

MULTI-LAYERED WOUND DRESSING

This application claims the benefit of priority of United Kingdom Patent Application No. GB 0017080.3, filed on Jul. 12, 2000, the entire contents of which are herein incorporated by reference.

FIELD OF THE INVENTION

The present invention relates to a multi layered wound dressing particularly, but not exclusively, for use as a dressing on highly exuding wounds located on areas of the body that require a high degree of flexibility from the dressing.

BACKGROUND OF THE INVENTION

It is known to make wound dressings for use on heavily exuding wounds from materials with a high moisture vapour transmission rate (MVTR). Such dressings rely on exudate being taken up by the dressing and spread across much of the surface area of the dressing in order to ensure sufficient moisture evaporation. Examples of such dressings are ALLEVYN™ marketed in adhesive or non-adhesive versions by Smith and Nephew or TIELLE™ marketed by Johnson and Johnson. Such dressings are not designed to absorb and retain the exudate but manage the exudate by allowing the moisture present in the exudate to evaporate. A disadvantage of such dressings is that the lateral wicking of exudate is not contained and can cause normal skin surrounding the wound to macerate. A further disadvantage of such dressings is that the rapid loss of exudate can cause the wound to desiccate.

It is also known to make wound dressings for use on heavily exuding wounds from absorbent materials that absorb and retain exudate in the dressing. A disadvantage of such dressings is that they tend to be rather thick and not particularly conformable to those wounds located in areas requiring a high degree of flexibility from the dressing such as elbows and heels.

There is thus a need for a wound dressing which is capable of managing exudate at the rate it is produced by a wound and which also is able to conform to wound sites on highly contoured areas of the body such as elbows and heels.

SUMMARY OF THE INVENTION

The present invention is directed to a multi layered wound dressing. The dressing comprises an adhesive layer, an absorbent layer overlying the adhesive layer on the surface furthest from the wound, and a moisture transmitting cover layer overlying the absorbent layer. The dressing should have a total thickness of less than 1.5 mm. In one embodiment, the cover layer has a moisture vapour transmission rate of at least 500 gm2. In some embodiments, the adhesive layer is apertured and/or can comprise a mixture of hydrocolloids and polyisobutylene. In some embodiments, the absorbent layer can be of a carboxymethylated fabric.

It is to be understood that both the foregoing general description and the following detailed description are exemplary, but are not restrictive of the invention.

DETAILED DESCRIPTION OF THE INVENTION

We have now invented a multi layered wound dressing which alleviates the above problems by combining absorption and moisture transmission in a conformable format and there is provided by a first embodiment of the present invention a multi layered wound dressing comprising:

(1) an adhesive layer,
(2) an absorbent layer overlying said adhesive layer on the surface furthest from the wound, and
(3) a moisture transmitting cover layer overlying the absorbent layer, the dressing having a total thickness of less than 1.5 mm.

Preferably the total thickness of the dressing is between 0.3 to 1.5 mm, more preferably between 0.4 to 1.0 mm and most preferably between 0.5 to 0.8 mm.

Preferably the dressing has a fluid handling capacity of at least 2 g/10 cm2/24 hr, more preferably between 2 g/10 cm2/24 hr and 20 g/10 cm2/24 hr and most preferably between 4 g/10cm2/24 hr and 15 g/10 cm2/24 hr.

We have found that wound dressings according to the invention may mitigate the problems associated with the management of high levels of exudate produced by some wounds yet be readily conformable to highly contoured wound sites and not lead to desiccation of the wound. It is thought that this is in part achieved by the selection of the absorbent layer which provides absorbency and acts as a reservoir of moisture to deter wound desiccation, without adding to the bulk of the dressing. This allows the manufacture of a thin dressing which has the fluid handling capacity of a much thicker dressing.

Preferably the cover layer has a high MVTR. This allows moisture to evaporate from the dressing and in combination with the absorbent layer assists in the reduction of bulk in the dressing.

The cover layer of the present invention is preferably a layer having a MVTR of at least 3000 g/m$^2$/24 hr measured by the method described in 1993 BP Appendix XX J1 in or in the range of from 1000 g/m$^2$/24 hr to 10000 g/m$^2$/24 hr. The cover layer may be in the form of film or a film/foam laminate. Examples of film materials which may be used as cover layers include polyurethanes; polyureas; homo- and copolymers of vinyl acetate; polyethers; polymers comprising amide blocks; homo- and copolyesters; or a combination of two or more of these. A film/foam laminate which may be used as cover layer of a wound dressing of the invention is an expanded polyurethane foam laminated to a polyurethane film.

The absorbent layer is present to absorb exudate from the wound and provide a reservoir of moisture to deter wound desiccation. The layer preferably has an absorbency of at least 10 g/g sodium/calcium chloride solution BP, more preferably from 12 to 26 g/g and most preferably an absorbency of from 14 to 20 g/g. The absorbent layer is preferably fibrous and most preferably comprises gel forming fibres. The absorbent layer preferably has a thickness from 0.2 to 1.4 mm, more preferably from 0.35 to 0.95 mm and most preferably 0.4 to 0.65 mm.

The gel forming fibres are preferably chemically modified cellulosic fibres in the form of a fabric and in particular carboxymethylated cellulose fabrics as described in WO 00/01425 to Akzo Nobel UK Ltd. The carboxymethylated cellulosic fabrics preferably have a degree of substitution of between 0.12 and 0.35 as measured by IR spectroscopy and are made by carboxymethylating a woven or non-woven cellulose fabric such that the absorbency is increased.

The cellulosic fabric preferably consists solely of cellulosic fibre but may contain a proportion of non-cellulosic fibre but may contain a proportion of non-cellulosic textile fibre or of gel-forming fibre. The cellulosic fibre is of known kind and may comprise continuous filament yarn and/or staple fibre. The carboxymethylation is generally performed by contacting the fabric with strong alkali and a carboxymethylating agent such as chloroacetic acid in an aqueous system.

Another suitable gel forming fibre comprises alginate fibre. Alginate fibres may be used alone in the absorbent layer or in admixture with non-cellulosic textile fibre, with other gel-forming fibre such as carboxymethyl cellulose fibre, or with both. A particularly preferred such fibre is an absorbent, composite fibre comprising a matrix of from at least 10% to less than 50% by weight of water insoluble alginate, such as calcium alginate, having dispersed therein at least 40% by weight or another polysaccharide. Suitably, the other polysaccharide may be selected from the group comprising carboxymethyl cellulose, carboxyethyl cellulose, other derivatives of cellulose, cellulose, pectin, hyaluronic acid and chitosan.

A method for making such absorbent, composite fibres comprises the following steps:

i) adding sodium alginate and another polysaccharide to water to form a dope;

ii) forcing the dope through a spinneret to form fibres;

iii) treating the resulting fibres with a source of ions to convert the alginate to water insoluble alginate and cross-link the alginate to the other polysaccharide;

iv) drying the fibres.

The adhesive layer of the present invention forms the wound contacting surface of the dressing and adheres the dressing to the skin. Preferably the adhesive composition comprises a homogenous blend of one or more water soluble hydrocolloids and one or more low molecular weight polyisobutylenes such as are described in EP-B-92999 incorporated herein by reference. The water soluble hydrocolloids may be selected from sodium carboxymethylcellulose, pectin, gelatin, guar gum, locust bean gum, gum karaya, and mixtures thereof. The polyisobutylenes may be selected from low molecular weight polyisobutylenes having a viscosity average molecular weight of from 36,000 to 58,000 (Florey). The adhesive layer is capable of absorbing exudate while maintaining adhesion of the dressing to the skin.

Alternatively the adhesive composition may comprise a homgeneous blend of one or more hydrocolloids, one or more low molecular weight polyisobutylenes, one or more styrene block copolymers, mineral oil, butyl rubber, a tackifier and small amounts of optional components. By selection of specific ranges of the amounts of the above listed components, adhesive compositions may be prepared having good adhesion to the skin and stretchability. Such compositions and the preparation thereof are disclosed in EP-B-130061 incorporated herein by reference.

The adhesive composition may also comprise reinforcing fibres such as described in EP-B-130061 and EP-A-621042 to aid in the maintenance of the structural integrity of the dressing. Preferably the reinforcing fibres are present at a level of from 2% to 10% by weight of the adhesive composition. The adhesive layer may be substantially free from apertures; alternatively, it may include a plurality, preferably as a regular array, of apertures from 0.25 to 10 mm in diameter, especially from 5 to 8 mm in diameter.

The composition may be in form of a layer of the island type where different regions of the adhesive layer have different properties. For example the adhesive layer could comprise a central zone of swellable material backed and surrounded by a more rigid adhesive or the adhesive layer could be apertured to allow rapid uptake of exudate into the dressing.

The dressing will typically be made in three sizes, 55 mm×55 mm square, 105×105 mm square and 205×105 mm rectangular, all dressings preferably being about 0.6 mm thick.

Preferred embodiments of the invention will now be illustrated in the following examples.

Example 1

A multi layered dressing according to the invention was made by obtaining an absorbent layer as described in WO 00/01425 having a low degree of substitution and in the form of a hydroentangled apertured fabric and bonding it to a polyurethane film coated with an adhesive by conventional heat lamination/pressure techniques.

An adhesive is applied by extrusion in the correct dimensions onto silicone release paper and then transferred onto the absorbent layer of the dressing, either prior to or subsequent to the heat sealing process. In this way the adhesive is keyed into the absorbent layer via conventional pressure/heat lamination techniques. The dressings were press cut or roller cut from the laminated web.

Example 2

The fluid handling characteristics of various embodiments of the present invention were compared to a commercially available thin dressing.

| Dressing | Total Dressing Thickness (mm) | Moisture vapour Transmission (g) | Fluid Absorbed (g) | Fluid handling Capacity (g) |
| --- | --- | --- | --- | --- |
| Example 1 with fabric absorbent layer omitted | Approx 0.5-0.6 | 2.47 | 2.03 | 4.50 |
| Example 1 with fabric absorbent layer omitted and apertured adhesive | 0.55 | 3.60 | 1.78 | 5.38 |
| Example 1 | 0.79 | 2.05 | 2.25 | 4.30 |
| Example 1 with apertured adhesive | 0.84 | 5.62 | 2.41 | 8.03 |
| DuoDERM Extra Thin | 0.66 | 0.23 | 1.26 | 1.49 |

Moisture vapour transmission, fluid absorbed and total fluid handling are measured as per BP, 1996, monograph for hydrocolloid dressings, fluid handling test.

Example 3

A multi layered dressing was made as follows: the absorbent layer was placed onto a flat surface and coated with about 10 to 20 gms of co-polyamide powder bond material. The polyurethane film material (plus its support) was then placed onto this and the assembly passed through a fusing press at about 100 °C.

A sheet of hydrocolloid adhesive with 5 mm perforations was next placed onto the absorbent surface of the assembly and bonded (on the fusing press set at 80 °C). As previously explained in Example 1 the adhesive is now keyed-in to the dressing.

A fresh piece of release liner was placed across the hydrocolloid layer and the final dressing shape was cut out. The dressings were then packaged and irradiated at 35.5 kGy prior to testing.

Thickness determination of extra thin dressings with varying films applied.

| Sample | Thickness (mm) | Std. Dev. |
|---|---|---|
| Sample | 10.64 | 0.07 |
| Sample | 20.65 | 0.07 |
| Sample | 30.78 | 0.05 |

(n = 10).

What is claimed is:

1. A multi layered wound dressing which comprises:
an adhesive layer forming the wound contacting surface of the dressing and adhering the dressing to the skin;
a fibrous absorbent layer comprising a carboxymethylated cellulosic fabric overlying said adhesive layer on the surface of the adhesive layer furthest from the wound; and
a moisture transmitting cover layer overlying the fibrous absorbent layer, wherein the dressing has a total thickness of less than 1.5 mm, the absorbent layer exhibits an absorbency of at least 10 g/g sodium/calcium chloride solution BP and the dressing exhibits a fluid handling capacity of at least 2g/10 cm$^2$/24 hr.

2. The multi layered wound dressing of claim 1 wherein the adhesive layer is apertured.

3. The multi layered wound dressing of claim 1 wherein the adhesive layer comprises a mixture of hydrocolloids and polyisobutylene.

4. The multi layered wound dressing of claim 1 wherein the absorbent layer is from 0.2 to 1.4 mm in thickness.

5. The multi layered wound dressing of claim 1 wherein the absorbent layer is from 0.4 to 0.65 mm thickness.

6. The multi layered wound dressing of claim 1 wherein the cover layer has a moisture vapour transmission rate of at least 500 g/m$^2$/24 hr.

7. The multi layered wound dressing of claim 1 wherein the dressing exhibits a fluid handling capacity of between 2 g/10 cm$^2$/24 hr and 20 g/10 cm$^2$/24 hr.

8. The multi layered wound dressing of claim 1 wherein the dressing exhibits a fluid handling capacity of between 4 g/10 cm$^2$/24 hr and 15 g/10 cm$^2$/24 hr.

9. The multi layered wound dressing of claim 1 wherein the absorbent layer exhibits an absorbency of 12 to 26 g/g sodium/calcium chloride solution BP.

10. The multi layered wound dressing of claim 1 wherein the absorbent layer exhibits an absorbency of 14 to 20 g/g sodium/calcium chloride solution BP.

11. A multi layered wound dressing which comprises:
an adhesive layer forming the wound contacting surface of the dressing and adhering the dressing to the skin;
an absorbent layer overlying said adhesive layer on the surface of the adhesive layer furthest from the wound, wherein the absorbent layer is a carboxymethylated cellulosic fabric; and
a moisture transmitting cover layer overlying the absorbent layer,
wherein the dressing has a total thickness of less than 1.5 mm and the absorbent layer exhibits an absorbency of at least 10 g/g sodium/calcium chloride solution BP.

12. The multi layered wound dressing of claim 11 wherein the adhesive layer is apertured.

13. The multi layered wound dressing of claim 11 wherein the adhesive layer comprises a mixture of hydrocolloids and polyisobutylene.

14. The multi layered wound dressing of claim 11 wherein the absorbent layer is from 0.2 to 1.4 mm in thickness.

15. The multi layered wound dressing of claim 11 wherein the absorbent layer is from 0.4 to 0.65 mm in thickness.

16. The multi layered wound dressing of claim 11 wherein the cover layer has a moisture vapour transmission rate of at least 500 g/m$^2$/24 hr.

17. The multi layered wound dressing of claim 11 wherein the dressing exhibits a fluid handling capacity of between 2 g/10 cm$^2$/24 hr and 20 g/10 cm$^2$/24 hr.

18. The multi layered wound dressing of claim 11 wherein the dressing exhibits a fluid handling capacity of between 4 g/10 cm$^2$/24 hr and 15 g/10 cm$^2$/24 hr.

19. The multi layered wound dressing of claim 11 wherein the absorbent layer exhibits an absorbency of 12 to 26 g/g sodium/calcium chloride solution BP.

20. The multi layered wound dressing of claim 11 wherein the absorbent layer exhibits an absorbency of 14 to 20 g/g sodium/calcium chloride solution BP.

* * * * *